United States Patent [19]

Takematsu et al.

[11] Patent Number: 4,465,509
[45] Date of Patent: Aug. 14, 1984

[54] UREA COMPOUNDS AND HERBICIDAL COMPOSITIONS CONTAINING THEM

[75] Inventors: Tetsuo Takematsu; Yasutomo Takeuchi, both of Utsunomiya; Michiyuki Kohno, Maebashi; Akihiko Aoki, Tochigi; Nobuo Aoki, Shibukawa; Toshiro Watanuki, Shibukawa; Koichi Moriya, Shibukawa, all of Japan

[73] Assignee: The Japan Carlit Co., Ltd., Tokyo, Japan

[21] Appl. No.: 424,244

[22] Filed: Sep. 27, 1982

[30] Foreign Application Priority Data

Aug. 30, 1982 [JP] Japan ................. 57-150546
Aug. 30, 1982 [JP] Japan ................. 57-150547

[51] Int. Cl.³ .................. A01N 9/20; C07C 127/17
[52] U.S. Cl. ........................ 71/119; 71/120; 564/56
[58] Field of Search .............. 564/56; 71/119, 120

[56] References Cited

U.S. PATENT DOCUMENTS 3,004,035 10/1961 Csendes ..................... 564/56 X
4,039,577 8/1977 Yokoo et al. ............... 564/56 X
4,143,061 3/1979 Kubo et al. ................ 564/56 X

FOREIGN PATENT DOCUMENTS 1518688 3/1969 Fed. Rep. of Germany ........ 564/56
45-28504 4/1970 Japan ........................ 564/56
202927 1/1968 U.S.S.R. ..................... 564/56

Primary Examiner—Thomas A. Waltz
Attorney, Agent, or Firm—Frishauf, Holtz, Goodman & Woodward

[57] ABSTRACT

Compound of the formula,

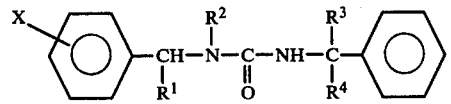

wherein X is a hydrogen atom, a halogen atom, a lower alkyl group or a lower alkoxyl group, $R^1$ is a methyl group or an ethyl group, $R^2$ is a hydrogen atom, a lower alkyl group or an allyl group, and each of $R^3$ and $R^4$, independently, is a hydrogen atom, a methyl group or an ethyl group; provided that $R^1$, $R^3$ and $R^4$ are not methyl groups simultaneously when both X and $R^2$ are hydrogen atoms, and compositions containing these compounds exhibit herbicidal activity.

24 Claims, No Drawings

UREA COMPOUNDS AND HERBICIDAL COMPOSITIONS CONTAINING THEM

BACKGROUND OF THE INVENTION

1. Field of the Invention

This invention relates to novel 1,3-dibenzylurea compounds and herbicidal compositions containing them as active ingredients and an agronomically acceptable carrier.

2. Description of Prior Art

Some compounds having chemical structures similar to the compounds of the invention have been reported and are well known in the art; e.g., 3-($\alpha,\alpha$-dimethylbenzyl)-1-(4-methylphenyl) urea (Control compound a in the examples presented subsequently), 1,3-bis($\alpha,\alpha$-dimethylbenzyl) urea (Control compound b in the examples presented subsequently) and 3-(2,4-dichloro-$\alpha,\alpha$-dimethylbenzyl)-1-($\alpha,\alpha$-dimethylbenzyl) urea (Control compound c in the examples presented subsequently). The control compounds a, b and c are described in Japanese Patent Publication No. 35454/1973, ibid. No. 41664/1978 and Japanese Patent Public Disclosure No. 83432/1977, respectively. According to our experiments, as some of the results are shown in the examples presented subsequently, the control compound a moderately harms paddy rice and shows slight herbicidal activities against perennial cyperaceous weeds such as water nutgrass and water chestnut, while the control compounds b and c do not harm paddy rice but control undesirable weeds only to minor extents.

SUMMARY OF THE INVENTION

It is an object of the invention to provide novel 1,3-dibenzylurea compounds.

It is another object of the invention to provide novel herbicidal compositions containing the novel 1,3-dibenzylurea compounds as active ingredients.

Other objects and advantages of the present invention may become apparent to those skilled in the art from the following description and disclosure.

DESCRIPTION OF THE PREFERRED EMBODIMENT

The compounds of this invention have the following general formula I:

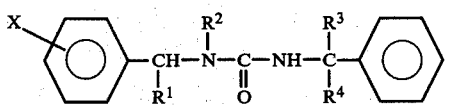

wherein X is a hydrogen atom, a halogen atom, a lower alkyl group or a lower alkoxyl group, $R^1$ is a methyl group or an ethyl group, $R^2$ is a hydrogen atom, a lower alkyl group or an allyl group, and each of $R^3$ and $R^4$, independently, is a hydrogen atom, a methyl group or an ethyl group; provided that $R^1$, $R^3$ and $R^4$ are not methyl groups simultaneously when both X and $R^2$ are hydrogen atoms.

In the above formula, the halogen atom can be a chlorine, bromine or fluorine; the lower alkyl group can be a methyl, ethyl, n-propyl, isopropyl, n-butyl or tert-butyl group; and the lower alkoxyl group can be a methoxyl or ethoxy group.

The compounds of formula I can be prepared, for example, by the following method: reacting an amine compound of formula II,

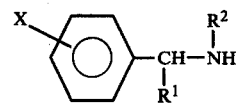

wherein X, $R^1$ and $R^2$ are as defined above with an isocyanate compound of formula III,

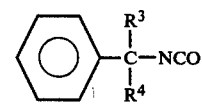

wherein $R^3$ and $R^4$ are as defined above.

These reactions are carried out without any solvents or in the presence of inert organic solvents such as benzene, toluene, xylene, acetone, tetrahydrofuran, 1,4-dioxane, dichloromethane, chloroform, tetrachloromethane, pyridine, N,N-dimethylformamide, methanol and ethanol, water or mixtures of water with the above organic solvents. The reactions are carried out at from room temperature to 50° C. for from one to five hours with or without basic catalysts. The product contained in the reaction mixture can be separated and purified by conventional means such as crystallization, distillation, adsorption, absorption, extractive distillation and any suitable combination of these.

Typical examples of the compounds of the invention embraced by formula I include:

1-(2-chloro-$\alpha$-methylbenzyl)-3-($\alpha,\alpha$-dimethylbenzyl) urea 1-(2-methyl-$\alpha$-methylbenzyl)-3-($\alpha,\alpha$-dimethylbenzyl) urea 1-($\alpha$-methylbenzyl)-1-methyl-3-($\alpha,\alpha$-dimethylbenzyl) urea 1-(2-chloro-$\alpha$-methylbenzyl)-1-methyl-3-($\alpha,\alpha$-dimethylbenzyl) urea 1-(2-chloro-$\alpha$-methylbenzyl)-1-(n-propyl)-3-($\alpha,\alpha$-dimethylbenzyl) urea 1-($\alpha$-methylbenzyl)-1-allyl-3-($\alpha,\alpha$-dimethylbenzyl) urea 1-(2-chloro-$\alpha$-methylbenzyl)-1-allyl-3-($\alpha,\alpha$-dimethylbenzyl) urea 1-($\alpha$-ethylbenzyl)-1-methyl-3-($\alpha,\alpha$-dimethylbenzyl) urea 1-(2-chloro-$\alpha$-methylbenzyl)-3-($\alpha$-ethyl-$\alpha$-methylbenzyl) urea 1-($\alpha$-methylbenzyl)-1-methyl-3-($\alpha$-ethyl-$\alpha$-methylbenzyl) urea 1-(2-methoxy-$\alpha$-methylbenzyl)-1-methyl-3-($\alpha$-ethyl-$\alpha$-methylbenzyl) urea 1-($\alpha$-methylbenzyl)-1-allyl-3-($\alpha$-ethyl-$\alpha$-methylbenzyl) urea 1-(2-chloro-$\alpha$-methylbenzyl)-1-allyl-3-($\alpha$-ethyl-$\alpha$-methylbenzyl) urea 1-(2-methyl-$\alpha$-methylbenzyl)-1-allyl-3-($\alpha$-ethyl-$\alpha$-methylbenzyl) urea 1-($\alpha$-methylbenzyl)-1-methyl-3-($\alpha,\alpha$-diethylbenzyl) urea 1-(2-chloro-$\alpha$-methylbenzyl)-1-methyl-3-($\alpha,\alpha$-diethylbenzyl) urea 1-(2-methyl-$\alpha$-methylbenzyl)-1-methyl-3-($\alpha,\alpha$-diethylbenzyl) urea 1-(2-chloro-α-methylbenzyl)-1-(n-propyl)-3-(α,α-diethylbenzyl) urea
1-(α-methylbenzyl)-1-allyl-3-(α,α-diethylbenzyl) urea
1-(2-methyl-α-methylbenzyl)-1-allyl-3-(α,α-diethylbenzyl) urea
1-(α-ethylbenzyl)-1-methyl-3-(α,α-diethylbenzyl) urea
1-(3-methyl-α-methylbenzyl)-3-(α,α-dimethylbenzyl) urea
1-(3-methyl-α-dimethylbenzyl)-1-methyl-3-(α,α-dimethylbenzyl) urea
1-(4-methyl-α-methylbenzyl)-1-methyl-3-(α,α-dimethylbenzyl) urea
1-(4-chloro-α-methylbenzyl)-1-ethyl-3-(α,α-dimethylbenzyl) urea
1-(3-methoxy-α-methylbenzyl)-1-allyl-3-(α,α-dimethylbenzyl) urea
1-(3-chloro-α-methylbenzyl)-1-methyl-3-(α-ethyl-α-methylbenzyl) urea
1-(4-chloro-α-methylbenzyl)-1-methyl-3-(α-ethyl-α-methylbenzyl) urea
1-(3-methyl-α-methylbenzyl)-1-methyl-3-(α-ethyl-α-methylbenzyl) urea
1-(4-methyl-α-methylbenzyl)-1-methyl-3-(α,α-diethylbenzyl) urea The following illustrate some methods of preparing the compounds of this invention.

A. Preparation of 1-(2-chloro-α-methylbenzyl)-1-(n-butyl)-3-(α,α-dimethylbenzyl) urea (Compound No. 16)

A mixture consisting of 8.1 g of α,α-dimethylbenzylisocyanate and 10.6 g of N-butyl-N-(2-chloro-α-methylbenzyl) amine was allowed to stand for 3 hours at room temperature. The product was isolated from the reaction mixture by column chromatography on silica gel using ethyl acetate-methylene chloride as a developing solvent and recovered as a colorless syrup weighing 15.3 g, $n_D^{25}$ 1.5451.

NMR: 0.8–1.4 (7H,m), 1.47 (3H,d), 1.60 (6H,s), 3.03 (2H,t), 4.50 (1H, s), 5.37 (1H,q), 7.0–7.5 (9H,m)

B. Preparation of 1-(2-methyl-α-methylbenzyl)-1-methyl-3-(α,α-diethylbenzyl) urea (Compound No. 42)

A mixture consisting of 9.5 g of α,α-diethylbenzylisocyanate and 7.5 g of N-(2-methyl-α-methylbenzyl)-N-methylamine was allowed to stand for 3 hours at room temperature. The white deposit formed was then filtered off. Washing with n-hexane and recrystallization from ethanol gave 15.9 g of the product, mp 93.0°–94.0° C.

NMR: 0.65 (12H,t), 1.16 (3H,t), 1.88 (8H,q), 2.55 (2H,q), 6.07 (2H,s), 6.9–7.4 (9H,m)

Table 1 illustrates physical data of the compounds of this invention represented by general formula I. It is not intended, of course, that this invention is to be limited thereto. In Table 1, Me is methyl group, Et is ethyl group, n-Pro. is n-propyl group, i-Pro. is isopropyl group, n-Bu is n-butyl group and t-Bu is tert-butyl group. Compound Nos. in Table 1 are used throughout in this specification.

TABLE 1

$$X-\underset{}{\bigcirc}-CH(R^1)-N(R^2)-C(=O)-NH-C(R^3)(R^4)-\bigcirc$$

| Comp. No. | X | $R^1$ | $R^2$ | $R^3$, $R^4$ | Melting pt. (°C.) or Refractive index | Elemental analysis[*1] or NMR[*2] |
|---|---|---|---|---|---|---|
| 1 | 2-Cl | Me | H | Me, Me | mp 167–168 | C: 67.20 (68.24) H: 6.69 (6.68) N: 8.80 (8.84) |
| 2 | 2-Me | Me | H | Me, Me | mp 164–166 | C: 75.94 (76.99) H: 8.21 (8.16) N: 9.55 (9.45) |
| 3 | 2-OMe | Me | H | Me, Me | mp 156–158 | C: 72.36 (73.05) H: 7.64 (7.74) N: 9.03 (8.97) |
| 4 | H | Me | Me | Me, Me | mp 106–108 | C: 77.58 (76.99) H: 8.19 (8.16) N: 9.52 (9.45) |
| 5 | 2-Cl | Me | Me | Me, Me | mp 130–132 | 1.33(3H,d), 1.50(3H,s) 1.53(3H,s), 2.57(3H,s) 5.40(1H,q), 5.93(1H,s) 7.0–7.5(9H,m) |
| 6 | 2-Me | Me | Me | Me, Me | mp 134 | 1.32(3H,d), 1.56(6H,d) 2.16(3H,s), 2.47(3H,s) 5.4(1H,q), 5.96(1H,s) 7.0–7.5(9H,m) |
| 7 | 2-OMe | Me | Me | Me, Me | $n_D^{25}$ 1.5530 | C: 73.84 (73.59) H: 7.99 (8.03) N: 8.54 (8.58) |
| 8 | H | Me | Et | Me, Me | | C: 76.41 (77.38) H: 8.34 (8.44) N: 9.01 (9.02) |
| 9 | 2-Cl | Me | Et | Me, Me | | C: 70.37 (69.65) H: 7.37 (7.31) N: 8.21 (8.12) |
| 10 | H | Me | n-Pro. | Me, Me | mp 59–62 | C: 77.27 (77.74) H: 8.76 (8.70) N: 8.55 (8.63) |
| 11 | 2-Cl | Me | n-Pro. | Me, Me | $n_D^{29}$ 1.5459 | C: 69.68 (70.28) H: 7.52 (7.58) |

TABLE 1-continued $$\text{X}-\underset{R^1}{\underset{|}{C}H}-\underset{|}{\overset{R^2}{N}}-\underset{\overset{||}{O}}{C}-NH-\underset{R^4}{\overset{R^3}{\underset{|}{C}}}-\text{phenyl}$$

| Comp. No. | X | $R^1$ | $R^2$ | $R^3$, | $R^4$ | Melting pt. (°C.) or Refractive index | Elemental analysis*1 or NMR*2 |
|---|---|---|---|---|---|---|---|
| 12 | H | Me | i-Pro. | Me, | Me | $n_D^{29}$ 1.5410 | N: 7.89 (7.81) C: 78.52 (77.74) H: 8.71 (8.70) |
| 13 | 2-Cl | Me | i-Pro. | Me, | Me | $n_D^{29}$ 1.5444 | N: 8.60 (8.63) C: 69.25 (70.28) H: 7.67 (7.58) |
| 14 | 2-Me | Me | i-Pro. | Me, | Me | $n_D^{25}$ 1.5387 | N: 7.86 (7.81) C: 78.57 (78.06) H: 8.90 (8.93) |
| 15 | 2-OMe | Me | i-Pro. | Me, | Me | $n_D^{24}$ 1.5360 | N: 8.23 (8.28) C: 73.87 (74.54) H: 8.56 (8.53) |
| 16 | 2-Cl | Me | n-Bu | Me, | Me | $n_D^{25}$ 1.5451 | N: 7.96 (7.90) 0.8–1.4(7H,m), 1.47(3H,d), 1.60(6H,s) 3.03(2H,t), 4.50(1H,s) 5.37(1H,q), 7.0–7.5(9H,m) |
| 17 | H | Me | t-Bu | Me, | Me | $n_D^{26}$ 1.5401 | C: 77.95 (78.06) H: 8.96 (8.93) N: 8.33 (8.28) |
| 18 | H | Me | Allyl | Me, | Me | $n_D^{29}$ 1.5508 | C: 78.96 (78.22) H: 8.02 (8.13) N: 8.64 (8.69) |
| 19 | 2-Cl | Me | Allyl | Me, | Me | $n_D^{28}$ 1.5527 | C: 71.46 (70.67) H: 7.14 (7.06) N: 7.79 (7.85) |
| 20 | 2-Me | Me | Allyl | Me, | Me | $n_D^{26}$ 1.5566 | C: 79.21 (78.53) H: 8.41 (8.39) N: 8.40 (8.33) |
| 21 | 2-OMe | Me | Allyl | Me, | Me | $n_D^{24}$ 1.5623 | C: 75.86 (74.97) H: 8.11 (8.01) N: 8.03 (7.95) |
| 22 | H | Et | H | Me, | Me | mp 178–181 | C: 77.65 (76.99) H: 8.08 (8.16) N: 9.45 (9.45) |
| 23 | H | Et | Me | Me, | Me | mp 83–85 | C: 78.37 (77.38) H: 8.41 (8.44) N: 9.01 (9.02) |
| 24 | 2-Cl | Me | H | Me, | Et | mp 193–194 | C: 69.13 (68.98) H: 6.97 (7.01) N: 8.45 (8.47) |
| 25 | H | Me | Me | Me, | Et | mp 101–104 | C: 76.66 (77.38) H: 8.34 (8.44) N: 9.10 (9.02) |
| 26 | 2-Me | Me | Me | Me, | Et | mp 1.07–1.09 | C: 78.22 (77.74) H: 8.80 (8.70) N: 8.58 (8.63) |
| 27 | 2-OMe | Me | Me | Me, | Et | $n_D^{26}$ 1.5487 | 0.62(3H,t), 1.2–2.1(8H, m), 2.61(3H,s), 3.60 3H,s), 4.90(1H,d), 5.30 (1H,q), 6.6–7.3(9H,m) |
| 28 | H | Me | n-Pro. | Me, | Et | $n_D^{28}$ 1.5378 | 0.4–1.0(6H,m), 1.1–2.3 (10H,m), 2.7–3.3(2H,m) 4.47(1H,s), 5.34(1H,q) 6.8–7.6(10H,m) |
| 29 | 2-Cl | Me | n-Pro. | Me, | Et | $n_D^{29}$ 1.5444 | C: 71.55 (70.85) H: 7.88 (7.84) N: 7.60 (7.51) |
| 30 | H | Me | i-Pro. | Me, | Et | $n_D^{27}$ 1.5440 | C: 77.08 (78.06) H: 8.86 (8.93) N: 8.35 (8.28) |
| 31 | 2-Cl | Me | i-Pro. | Me, | Et | $n_D^{27}$ 1.5451 | C: 71.80 (70.85) H: 7.91 (7.84) N: 7.51 (7.51) |
| 32 | 2-Me | Me | i-Pro. | Me, | Et | $n_D^{25}$ 1.5550 | C: 78.14 (78.37) H: 9.10 (9.15) N: 7.95 (7.95) |
| 33 | 2-OMe | Me | i-Pro. | Me, | Et | $n_D^{29}$ 1.5452 | C: 75.95 (74.96) H: 8.73 (8.75) |

TABLE 1-continued $$\underset{R^1}{\overset{X}{\text{Ph}}}\text{CH}-\underset{}{\overset{R^2}{N}}-\underset{\underset{O}{\parallel}}{C}-NH-\underset{R^4}{\overset{R^3}{C}}\text{Ph}$$

| Comp. No. | X | $R^1$ | $R^2$ | $R^3$, $R^4$ | Melting pt. (°C.) or Refractive index | Elemental analysis*1 or NMR*2 |
|---|---|---|---|---|---|---|
| 34 | 2-Cl | Me | n-Bu | Me, Et | $n_D^{26}$ 1.5465 | N: 7.60 (7.60) 0.46–2.13(20H,m) 4.48(1H,s), 5.4(1H,q) 6.9–7.5(9H,m) |
| 35 | H | Me | t-Bu | Me, Et | $n_D^{29}$ 1.5511 | C: 77.64 (78.37) H: 9.15 (9.15) N: 7.92 (7.95) |
| 36 | H | Me | Allyl | Me, Et | $n_D^{28}$ 1.5520 | C: 79.17 (78.53) H: 8.40 (8.39) N: 8.26 (8.33) |
| 37 | 2-Cl | Me | Allyl | Me, Et | $n_D^{23}$ 1.5495 | C: 71.39 (71.24) H: 7.24 (7.34) N: 7.54 (7.55) |
| 38 | 2-Me | Me | Allyl | Me, Et | $n_D^{26}$ 1.5477 | 0.68(3H,t), 1.1–2.1(8H, m), 2.18(3H,d), 3.46 (2H,d), 4.70(1H,d), 4.8–5.4(3H,m), 5.60(1H, q), 6.8–7.4(9H,m) |
| 39 | 2-F | Et | Et | Me, Et | $n_D^{29}$ 1.5457 | C: 75.14 (74.12) H: 8.19 (8.20) N: 7.81 (7.86) |
| 40 | H | Me | Me | Et, Et | $n_D^{28}$ 1.5530 | 0.62(6H,t), 1.36(3H,d) 2.00(4H,q), 2.49(3H,s) 4.49(1H,s), 5.46(1H,q) 6.9–7.3(10H,m) |
| 41 | 2-Cl | Me | Me | Et, Et | mp 83–85 | C: 70.60 (70.28) H: 7.54 (7.58) N: 7.90 (7.81) |
| 42 | 2-Me | Me | Me | Et, Et | mp 93–94 | 0.65(12H,t), 1.16(3H,t) 1.88(8H,q), 2.55(2H,q) 6.07(2H,s) 6.9–7.4(9H,m) |
| 43 | H | Me | n-Pro. | Et, Et | mp 75–76 | 0.3–0.9(9H,m), 1.0–1.6 (5H,m), 1.6–2.1(4H,m), 2.8–3.2(2H,m), 5.1–5.5 (2H,m), 7.0–7.5(10H,m) |
| 44 | 2-Cl | Me | n-Pro. | Et, Et | $n_D^{28}$ 1.5494 | C: 71.65 (71.39) H: 8.02 (8.07) N: 7.34 (7.24) |
| 45 | H | Me | i-Pro. | Et, Et | $n_D^{28}$ 1.5425 | C: 78.26 (78.37) H: 9.12 (9.15) N: 8.05 (7.95) |
| 46 | 2-Cl | Me | i-Pro. | Et, Et | $n_D^{27}$ 1.5481 | C: 72.14 (71.39) H: 8.03 (8.07) N: 7.17 (7.24) |
| 47 | 2-Me | Me | i-Pro. | Et, Et | $n_D^{28}$ 1.5430 | C: 78.77 (78.64) H: 9.44 (9.35) N: 7.56 (7.64) |
| 48 | 2-OMe | Me | i-Pro. | Et, Et | $n_D^{24}$ 1.5361 | 0.65(6H,t), 0.91(3H,d) 1.1–1.7(6H,m), 1.8–2.3 (4H,m), 3.68(3H,s) 3.2–4.2(1H,m), 4.70 (1H,s), 5.28(1H,q) 6.6–7.4(9H,m) |
| 49 | 2-Cl | Me | n-Bu | Et, Et | $n_D^{24}$ 1.5347 | C: 72.36 (71.89) H: 8.33 (8.29) N: 7.08 (6.99) |
| 50 | H | Me | t-Bu | Et, Et | $n_D^{26}$ 1.5388 | C: 78.46 (78.64) H: 9.28 (9.35) N: 7.69 (7.64) |
| 51 | H | Me | Allyl | Et, Et | $n_D^{29}$ 1.5432 | 0.64(6H,t), 1.41(3H,d) 2.06(4H,q), 3.56(2H,d) 4.60(1H,s), 4.9–5.9(4H, m), 6.9–7.4(10H,m) |
| 52 | 2-Me | Me | Allyl | Et, Et | $n_D^{25}$ 1.5359 | C: 78.52 (79.08) H: 8.95 (8.85) N: 7.64 (7.68) |
| 53 | H | Et | Me | Et, Et | mp 88–89 | C: 79.04 (78.06) H: 8.98 (8.93) N: 8.23 (8.28) |
| 54 | 2-F | Et | Et | Et, Et | $n_D^{31}$ 1.5412 | C: 74.14 (74.56) |

TABLE 1-continued $$X-C_6H_4-CH(R^1)-N(R^2)-C(=O)-NH-C(R^3)(R^4)-C_6H_5$$

| Comp. No. | X | $R^1$ | $R^2$ | $R^3$, | $R^4$ | Melting pt. (°C.) or Refractive index | Elemental analysis*1 or NMR*2 |
|---|---|---|---|---|---|---|---|
| 55 | 3-Cl | Me | H | Me, | Me | mp 150–151 | H: 8.49 (8.43)<br>N: 7.46 (7.56)<br>1.40(3H,d), 1.57(3H,s)<br>1.63(3H,s), 2.63(3H,s)<br>6.20(1H,s), 5.43(1H,q) |
| 56 | 4-Cl | Me | H | Me, | Me | mp 145–146 | C: 67.65 (68.24)<br>H: 6.71 (6.68)<br>N: 8.81 (8.84) |
| 57 | 3-Me | Me | H | Me, | Me | mp 138 | C: 77.58 (76.99)<br>H: 8.21 (8.16)<br>N: 9.53 (9.45) |
| 58 | 4-Me | Me | H | Me, | Me | mp 139–140 | C: 77.55 (76.99)<br>H: 8.16 (8.16)<br>N: 9.37 (9.45) |
| 59 | 3-OMe | Me | H | Me, | Me | mp 130–131 | C: 72.05 (73.05)<br>H: 7.84 (7.74)<br>N: 8.94 (8.97) |
| 60 | 4-OMe | Me | H | Me, | Me | mp 132–134 | 1.25(3H,d), 1.52(6H,s)<br>3.72(3H,s), 4.3–4.7<br>(1H,m), 5.9–6.3(2H,m)<br>6.7–7.4(9H,m) |
| 61 | 3-Cl | Me | Me | Me, | Me | mp 95–96 | C: 68.21 (68.98)<br>H: 7.01 (7.01)<br>N: 8.46 (8.47) |
| 62 | 4-Cl | Me | Me | Me, | Me | mp 87–88 | 1.37(3H,d), 1.60(6H,s)<br>2.60(3H,s), 5.40(1H,q)<br>6.13(1H,s)<br>7.0–7.5(9H,m) |
| 63 | 3-Me | Me | Me | Me, | Me | mp 96–98 | C: 76.46 (77.38)<br>H: 8.45 (8.44)<br>N: 9.05 (9.02) |
| 64 | 4-Me | Me | Me | Me, | Me | mp 94–95 | C: 78.46 (77.38)<br>H: 8.43 (8.44)<br>N: 9.04 (9.02) |
| 65 | 3-OMe | Me | Me | Me, | Me | mp 79–81 | C: 74.15 (73.59)<br>H: 8.11 (8.03)<br>N: 8.48 (8.58) |
| 66 | 4-OMe | Me | Me | Me, | Me |  | C: 72.84 (73.59)<br>H: 7.96 (8.03)<br>N: 8.51 (8.58) |
| 67 | 3-Cl | Me | Et | Me, | Me | mp 66–68 | C: 69.09 (69.65)<br>H: 7.26 (7.31)<br>N: 8.08 (8.12) |
| 68 | 4-Cl | Me | Et | Me, | Me | $n_D^{27}$ 1.5471 | C: 69.69 (69.65)<br>H: 7.21 (7.31)<br>N: 8.19 (8.12) |
| 69 | 4-Me | Me | i-Pro. | Me, | Me | $n_D^{29}$ 1.5323 | C: 77.42 (78.06)<br>H: 8.94 (8.93)<br>N: 8.19 (8.28) |
| 70 | 3-OMe | Me | i-Pro. | Me, | Me | $n_D^{26}$ 1.5381 | C: 74.38 (74.54)<br>H: 8.51 (8.53)<br>N: 7.93 (7.90) |
| 71 | 4-OMe | Me | i-Pro. | Me, | Me | $n_D^{24}$ 1.5353 | C: 73.55 (74.54)<br>H: 8.47 (8.53)<br>N: 7.80 (7.90) |
| 72 | 4-Me | Me | Allyl | Me, | Me | $n_D^{26}$ 1.5490 | C: 78.76 (78.53)<br>H: 8.28 (8.39)<br>N: 8.31 (8.33) |
| 73 | 3-OMe | Me | Allyl | Me, | Me | $n_D^{24}$ 1.5472 | C: 74.93 (74.97)<br>H: 8.05 (8.01)<br>N: 7.88 (7.95) |
| 74 | 4-Cl | Et | H | Me, | Me | mp 160–162 | C: 69.70 (68.98)<br>H: 6.92 (7.01)<br>N: 8.51 (8.47) |
| 75 | 4-Cl | Et | Me | Me, | Me | $n_D^{26}$ 1.5681 | C: 70.58 (69.65)<br>H: 7.35 (7.31)<br>N: 8.19 (8.12) |
| 76 | 3-Cl | Me | Me | Me, | Et |  | C: 69.20 (69.65)<br>H: 7.21 (7.31)<br>N: 8.04 (8.12) |

TABLE 1-continued $$\text{X} - \underset{R^1}{\underset{|}{\text{C}}H} - \underset{R^2}{\underset{|}{N}} - \underset{\underset{O}{\|}}{C} - NH - \underset{R^4}{\underset{|}{C}} - \text{(phenyl)}$$
with R³ on C

| Comp. No. | X | R¹ | R² | R³, | R⁴ | Melting pt. (°C.) or Refractive index | Elemental analysis*¹ or NMR*² |
|---|---|---|---|---|---|---|---|
| 77 | 4-Cl | Me | Me | Me, | Et | mp 130–132 | 0.62(3H,t), 1.2–2.1 (8H,m), 2.61(3H,s) 3.60(3H,s), 4.90(1H,d) 5.30(1H,q) 6.6–7.3(9H,m) |
| 78 | 3-Me | Me | Me | Me, | Et | | C: 77.05 (77.74) H: 8.59 (8.70) N: 8.61 (8.63) |
| 79 | 4-Me | Me | Me | Me, | Et | mp 122–124 | C: 78.77 (77.74) H: 8.70 (8.70) N: 8.65 (8.63) |
| 80 | 3-OMe | Me | Me | Me, | Et | | C: 74.99 (74.08) H: 8.28 (8.29) N: 8.19 (8.23) |
| 81 | 4-Br | Me | Et | Me, | Et | $n_D^{26}$ 1.5634 | C: 63.00 (62.53) H: 6.64 (6.75) N: 6.91 (6.94) |
| 82 | 4-Et | Me | Et | Me, | Et | $n_D^{27}$ 1.5433 | C: 78.52 (78.37) H: 9.22 (9.15) N: 7.91 (7.95) |
| 83 | 4-Me | Me | i-Pro. | Me, | Et | $n_D^{29}$ 1.5313 | C: 78.21 (78.37) H: 9.10 (9.15) N: 8.00 (7.95) |
| 84 | 3-OMe | Me | i-Pro. | Me, | Et | $n_D^{26}$ 1.5381 | C: 74.48 (74.96) H: 8.66 (8.75) N: 7.70 (7.60) |
| 85 | 4-Me | Me | Allyl | Me, | Et | $n_D^{26}$ 1.5465 | C: 78.24 (78.82) H: 8.65 (8.63) N: 7.97 (7.99) |
| 86 | 3-OMe | Me | Allyl | Me, | Et | $n_D^{26}$ 1.5496 | C: 74.86 (75.38) H: 8.28 (8.25) N: 7.67 (7.64) |
| 87 | 4-OEt | Et | Et | Me, | Et | $n_D^{27}$ 1.5221 | C: 75.50 (75.35) H: 9.06 (8.96) N: 7.23 (7.32) |
| 88 | 3-Cl | Me | Me | Et, | Et | mp 97–98 | C: 70.94 (70.28) H: 7.50 (7.58) N: 7.85 (7.81) |
| 89 | 4-Cl | Me | Me | Et, | Et | mp 89–90 | 0.62(6H,t), 1.36(3H,d) 1.95(4H,q), 2.60(3H,s) 5.38(1H,q), 5.60(1H,s) 7.0–7.5(9H,m) |
| 90 | 3-Me | Me | Me | Et, | Et | mp 67–69 | C: 77.35 (78.06) H: 8.88 (8.93) N: 8.21 (8.28) |
| 91 | 4-Me | Me | Me | Et, | Et | mp 81–82 | C: 77.86 (78.06) H: 8.97 (8.93) N: 8.29 (8.28) |
| 92 | 3-OMe | Me | Me | Et, | Et | mp 75–76 | 0.63(6H,t), 1.37(3H,d) 2.02(4H,q), 2.53(3H,s) 3.65(3H,s), 4.53(1H,s) 5.43(1H,q) 6.5–7.3(9H,m) |
| 93 | 4-Br | Me | Et | Et, | Et | $n_D^{29}$ 1.5606 | C: 63.68 (63.31) H: 7.03 (7.00) N: 6.68 (6.71) |
| 94 | 4-Et | Me | Et | Et, | Et | $n_D^{25}$ 1.5401 | C: 78.24 (78.64) H: 9.27 (9.35) N: 7.74 (7.64) |
| 95 | 4-Me | Me | i-Pro. | Et, | Et | $n_D^{25}$ 1.5519 | C: 78.02 (78.64) H: 9.35 (9.35) N: 7.69 (7.64) |
| 96 | 3-OMe | Me | i-Pro. | Et, | Et | $n_D^{25}$ 1.5334 | C: 75.53 (75.35) H: 9.06 (8.96) N: 7.38 (7.32) |
| 97 | 4-Me | Me | Allyl | Et, | Et | $n_D^{25}$ 1.5397 | C: 78.71 (79.08) H: 8.74 (8.85) N: 7.78 (7.68) |
| 98 | 3-OMe | Me | Allyl | Et, | Et | $n_D^{25}$ 1.5397 | 0.67(6H,t), 1.43(3H,d) 2.07 (4H,q), 3.5–3.8 (2H,m), 3.73(3H,s) |

TABLE 1-continued $$\text{X}-\underset{}{\bigcirc}-\underset{R^1}{\overset{}{\text{CH}}}-\underset{}{\overset{R^2}{\underset{}{\text{N}}}}-\underset{\underset{O}{\|}}{\text{C}}-\text{NH}-\underset{R^4}{\overset{R^3}{\underset{}{\text{C}}}}-\bigcirc$$

| Comp. No. | X | $R^1$ | $R^2$ | $R^3$, | $R^4$ | Melting pt. (°C.) or Refractive index | Elemental analysis[*1] or NMR[*2] |
|---|---|---|---|---|---|---|---|
| 99 | 4-Cl | Et | Me | Et, | Et | mp 109–110 | 4.70(1H,s), 4.9–6.1 (3H,m), 5.60(1H,q) 6.5–7.2(9H,m) 0.68(6H,t), 0.78(3H,t) 1.6–2.2(6H,m), 2.53(3H,s), 5.1(1H,t) 5.63(1H,s) 6.9–7.5(9H,m) |
| 100 | 4-OEt | Et | ET | Et, | Et | $n_D^{27}$ 1.5354 | C:76.23 (75.72) H: 9.11 (9.15) N: 7.06 (7.06) |

[*1]In parentheses, calculated values are designated.
[*2]Measured at 60 MHz, using dimethyl sulfoxide-$d_6$ as solvent and tetra-methylsilane as an internal standard. The numerical values are the chemical shifts (δ in ppm), s,d,t,q and m indicating singlet, doublet, triplet, quadruplet and multiplet, respectively.

The compounds of this invention have an unexpectedly high degree of selective activities as herbicides and control a wide variety of lowland weeds such as barnyardgrass, umbrellaplants, monochoria, spike-flowered rotala and false pimpernel. An outstanding feature of the compounds of this invention is that they exert a strong herbicidal action against perennial cyperaceous weeds such as water nutgrass, water chestnut and slender-spikerush which are very difficult to control with conventional herbicides and, on the other hand, they do not harm paddy rice whatever the cultivation method such as direct sowing in flooded paddy field, direct sowing in well-drained paddy field, sowing in flooded paddy field or transplanting of seedlings. A further outstanding feature of the compounds of this invention is that they have herbicidal activities against upland weeds such as watergrass, small watergrass, large crabgrass, green foxtail, yellow-cyperus, nutgrass, green kyllinga, green amaranth, fat hen, posumbu knotweed and China jute, particularly potent in the case of soil surface treatments, soil incorporations and foliar treatments while being harmless to crop plants such as wheat, rice, corn, cotton, soybean, sunflower and peanut by any methods of treatment described above and to vegetables such as eggplant, cucumber and tomato.

The compounds of this invention, as described above, differ from the aforementioned similar compounds in having unexpected features such as selectively killing perennial cyperaceous weeds, e.g., water nutgrass and water chestnut, without harming beneficial plants, e.g., paddy rice and corn. It is well known that selectively killing undesirable weeds alone is a very important feature in herbicides.

The herbicidal compositions of this invention can be widely used in various fields such as paddy rice, cereal crop, forage crop, oil crop and vegetable fields as well as tea gardens, orchards, mulberry fields, lawns, forests and non-crop fields.

The herbicidal compositions of this invention can be used not only in the form of pure chemicals, but, for practical uses as herbicides, in the form of mixtures with agronomically-acceptable carriers prepared in the form of granules, fine granules, wettable powders, emulsifiable concentrates, water soluble concentrates, dusts, crude dusts and tablets, depending on the nature of the fields of application. Examples of solid carriers are mineral powders such as calcium carbonates, apatite gypsum, silica gel, vermiculite, mica, diatomaceous earth, talc, pyrophyllite, acid clay, clay, kaolinite, montmorillonite, bentonite, zieclite and white carbon; plant powders such as crystalline cellulose and starch; and high molecular compounds such as poly(vinyl chloride) and petroleum resin. Examples of liquid carriers are alcohols such as methanol, etheralcohols such as ethylene glycol monoethyl ether, nitriles such as acetonitrile, acid amides such as N,N-dimethylformamide, ethers such as 1,4-dioxane and tetrahydrofuran, esters such as ethyl acetate, ketones such as acetone, chlorinated hydrocarbons such as chloroform and tetrachloromethane, aromatic hydrocarbons such as toluene, xylene, benzene, methylnaphtalene and chlorobenzene, other organic solvents such as dimethyl sulfoxide and isophorone, water and mixtures of water with any of the above organic solvents. Each of these carriers can be used alone or admixed with others. Wetting agents, dispersing agents, emulsifying agents, spreading agents, adhesive agents and forming agents can also be used as auxiliary substances in the above preparation.

The herbicidal compositions of this invention can also be used together with pesticides such as other herbicides, insecticides, fungicides and plant growth regulators or agricultural materials such as fertilizers and soil conditioning agents by pre-mixing or simultaneous applications.

In order to illustrate the preparation of the herbicidal compositions of this invention, the following examples are given. All parts are given by weight unless otherwise indicated.

EXAMPLE 1

Preparation of a wettable powder

Twenty-five parts of compound No. 1, 70 parts of talc, 2 parts of an alkylarylsulfonate and 3 parts of SORPOR800A (a surfactant made by Toho Chemical Ind. Co., Ltd.) were mixed and pulverized to give a wettable powder.

EXAMPLE 2

Preparation of a granular composition

A mixture of 5 parts of compound No. 2, 90 parts of bentonite and 5 parts of a sodium ligninsulfonate was mixed with water to make granules, which were then dried to give a granular composition.

The herbicidal activities of the compounds of this invention are more fully illustrated by the following examples.

EXAMPLE 3

Soil treatment test under flooded condition

Paddy field soil was charged into a Wagner pot of 1/5000 are, seeds of barnyardgrass, three-squaregrass and umbrellaplant were sowed in the pot and admixed with the surface soil, two seedlings of paddy rice and two tubers of water nutgrass were transplanted thereto and then the pot was filled with water up to a depth of about 3 cm over the soil. A wettable powder containing 25% of each test compound, prepared as in the above Example 1, was dispersed in water and applied by dripping on to the surface of water at a rate of 50 g.-a.i./10a. The pot was placed in a green house. On the 21st day after treatment, average herbicidal activities against weeds and phytotoxicity against paddy rice of the test compound were evaluated on a numerical scale of from 0 to 5 as defined in the following Table 2:

TABLE 2

| Scale | Herbicidal activity (percent damage) | Phytotoxicity to crop |
|---|---|---|
| 5 | 81–100 | Kill |
| 4 | 61–80 | Severe damage |
| 3 | 41–60 | Considerable damage |
| 2 | 21–40 | Moderate damage |
| 1 | 11–20 | Slight damage |
| 0 | 0–10 | No damage |

The results are given in the following Table 3.

TABLE 3

| Test Comp. No. | Phytotoxicity to rice | Barnyardgrass | Threesquaregrass | Umbrellaplant | Water nutgrass | Slenderspikerush | Monochoria |
|---|---|---|---|---|---|---|---|
| 1 | 0 | 3 | 5 | 5 | 5 | 5 | 2 |
| 2 | 0 | 5 | 5 | 5 | 5 | 5 | 1 |
| 3 | 0 | 4 | 1 | 0 | 1 | 2 | 0 |
| 4 | 0 | 4 | 5 | 5 | 5 | 5 | 2 |
| 5 | 0 | 4 | 5 | 5 | 4 | 5 | 3 |
| 6 | 0 | 5 | 5 | 5 | 5 | 5 | 1 |
| 7 | 0 | 5 | 5 | 5 | 5 | 5 | 4 |
| 8 | 0 | 4 | 5 | 4 | 4 | 4 | 3 |
| 9 | 0 | 4 | 5 | 4 | 4 | 5 | 3 |
| 10 | 0 | 4 | 2 | 3 | 1 | 2 | 0 |
| 11 | 0 | 5 | 5 | 5 | 5 | 5 | 1 |
| 12 | 0 | 3 | 4 | 3 | 3 | 4 | 1 |
| 13 | 0 | 3 | 3 | 2 | 1 | 2 | 1 |
| 14 | 0 | 2 | 2 | 0 | 0 | 2 | 2 |
| 15 | 0 | 2 | 5 | 4 | 3 | 4 | 1 |
| 16 | 0 | 5 | 5 | 5 | 5 | 5 | 4 |
| 17 | 0 | 2 | 5 | 5 | 5 | 5 | 0 |
| 18 | 0 | 5 | 5 | 5 | 5 | 5 | 2 |
| 19 | 0 | 5 | 5 | 5 | 5 | 4 | 4 |
| 20 | 0 | 5 | 4 | 3 | 5 | 4 | 1 |
| 21 | 0 | 5 | 3 | 5 | 4 | 4 | 1 |
| 22 | 0 | 1 | 5 | 5 | 5 | 5 | 5 |
| 23 | 0 | 4 | 5 | 5 | 5 | 5 | 0 |
| 24 | 0 | 5 | 5 | 5 | 5 | 5 | 4 |
| 25 | 0 | 5 | 5 | 5 | 5 | 5 | 2 |
| 26 | 0 | 4 | 4 | 4 | 4 | 5 | 2 |
| 27 | 0 | 5 | 5 | 5 | 5 | 5 | 1 |
| 28 | 0 | 3 | 1 | 4 | 3 | 4 | 1 |
| 29 | 0 | 4 | 5 | 5 | 4 | 3 | 0 |
| 30 | 0 | 4 | 3 | 3 | 2 | 2 | 0 |
| 31 | 0 | 4 | 4 | 4 | 2 | 2 | 0 |
| 32 | 0 | 5 | 5 | 5 | 4 | 5 | 1 |
| 33 | 0 | 1 | 5 | 5 | 3 | 4 | 3 |
| 34 | 0 | 2 | 5 | 4 | 3 | 2 | 2 |
| 35 | 0 | 1 | 4 | 5 | 3 | 3 | 5 |
| 36 | 0 | 2 | 5 | 5 | 3 | 4 | 5 |
| 37 | 0 | 3 | 5 | 5 | 4 | 4 | 5 |
| 38 | 0 | 3 | 5 | 5 | 3 | 1 | 3 |
| 39 | 0 | 5 | 5 | 3 | 1 | 2 | 0 |
| 40 | 0 | 5 | 5 | 5 | 5 | 5 | 3 |
| 41 | 0 | 5 | 2 | 5 | 3 | 3 | 1 |
| 42 | 0 | 2 | 4 | 5 | 5 | 4 | 1 |
| 43 | 0 | 1 | 0 | 4 | 3 | 4 | 3 |
| 44 | 0 | 0 | 5 | 5 | 3 | 4 | 1 |
| 45 | 0 | 4 | 5 | 5 | 2 | 2 | 2 |
| 46 | 0 | 0 | 2 | 1 | 0 | 1 | 5 |
| 47 | 0 | 1 | 0 | 2 | 0 | 2 | 0 |
| 48 | 0 | 3 | 5 | 4 | 3 | 2 | 3 |
| 49 | 0 | 2 | 5 | 3 | 2 | 4 | 4 |
| 50 | 0 | 0 | 3 | 2 | 2 | 2 | 2 |
| 51 | 0 | 3 | 5 | 5 | 4 | 4 | 1 |
| 52 | 0 | 2 | 4 | 3 | 3 | 4 | 2 |
| 53 | 0 | 4 | 5 | 5 | 5 | 4 | 2 |
| 54 | 0 | 3 | 4 | 2 | 2 | 3 | 1 |
| 55 | 0 | 3 | 4 | 3 | 4 | 4 | 3 |
| 56 | 0 | 2 | 5 | 5 | 5 | 3 | 1 |
| 57 | 0 | 5 | 4 | 5 | 4 | 5 | 2 |
| 58 | 0 | 3 | 3 | 5 | 5 | 4 | 3 |
| 59 | 0 | 3 | 1 | 0 | 0 | 1 | 0 |
| 60 | 0 | 4 | 2 | 0 | 1 | 0 | 0 |
| 61 | 0 | 5 | 5 | 5 | 5 | 5 | 4 |
| 62 | 0 | 5 | 5 | 5 | 5 | 5 | 4 |
| 63 | 0 | 5 | 5 | 5 | 4 | 5 | 1 |
| 64 | 0 | 5 | 5 | 5 | 5 | 5 | 2 |
| 65 | 0 | 5 | 5 | 5 | 5 | 5 | 1 |
| 66 | 0 | 3 | 4 | 3 | 3 | 4 | 2 |
| 67 | 0 | 5 | 5 | 4 | 5 | 5 | 4 |
| 68 | 0 | 4 | 5 | 4 | 4 | 5 | 4 |
| 69 | 0 | 2 | 5 | 2 | 1 | 2 | 3 |
| 70 | 0 | 2 | 4 | 2 | 3 | 4 | 3 |
| 71 | 0 | 2 | 5 | 3 | 3 | 5 | 2 |
| 72 | 0 | 5 | 4 | 5 | 3 | 3 | 0 |
| 73 | 0 | 4 | 5 | 5 | 5 | 5 | 4 |
| 74 | 0 | 1 | 4 | 4 | 4 | 5 | 3 |
| 75 | 0 | 5 | 5 | 5 | 5 | 5 | 3 |
| 76 | 0 | 5 | 5 | 5 | 4 | 5 | 3 |
| 77 | 0 | 5 | 2 | 2 | 3 | 2 | 1 |
| 78 | 0 | 4 | 5 | 5 | 5 | 4 | 2 |
| 79 | 0 | 2 | 4 | 3 | 3 | 4 | 2 |
| 80 | 0 | 2 | 3 | 2 | 2 | 3 | 1 |
| 81 | 0 | 5 | 4 | 5 | 4 | 3 | 1 |
| 82 | 0 | 4 | 3 | 3 | 3 | 4 | 2 |
| 83 | 0 | 2 | 5 | 5 | 4 | 4 | 2 |
| 84 | 0 | 1 | 3 | 5 | 5 | 5 | 5 |
| 85 | 0 | 2 | 2 | 4 | 2 | 2 | 3 |
| 86 | 0 | 0 | 2 | 3 | 1 | 1 | 2 |
| 87 | 0 | 5 | 2 | 3 | 1 | 1 | 1 |
| 88 | 0 | 4 | 3 | 5 | 4 | 4 | 2 |
| 89 | 0 | 0 | 2 | 5 | 5 | 5 | 3 |
| 90 | 0 | 3 | 4 | 5 | 4 | 3 | 1 |
| 91 | 0 | 2 | 4 | 5 | 4 | 3 | 2 |
| 92 | 0 | 2 | 3 | 5 | 3 | 4 | 3 |
| 93 | 0 | 3 | 4 | 5 | 3 | 3 | 2 |
| 94 | 0 | 5 | 3 | 3 | 2 | 2 | 2 |
| 95 | 0 | 5 | 2 | 1 | 0 | 1 | 0 |
| 96 | 0 | 3 | 5 | 5 | 4 | 3 | 2 |
| 97 | 0 | 3 | 5 | 5 | 4 | 4 | 0 |
| 98 | 0 | 2 | 5 | 5 | 4 | 5 | 3 |
| 99 | 0 | 0 | 1 | 2 | 1 | 2 | 2 |
| 100 | 0 | 4 | 4 | 2 | 2 | 2 | 0 |
| a ① | 2 | 3 | 4 | 4 | 1 | 3 | 2 |
| b ② | 0 | 2 | 3 | 3 | 2 | 2 | 1 |

TABLE 3-continued

| Test Comp. No. | Phyto-toxicity to rice | Herbicidal activity | | | | | |
|---|---|---|---|---|---|---|---|
| | | Barn-yard-grass | Three-square-grass | Um-brel-la-plant | Wa-ter nut-grass | Slender-spike-rush | Mono-choria |
| c ③ | 0 | 2 | 2 | 3 | 2 | 2 | 0 |

① - ③ : control compounds a, b and c described above.

EXAMPLE 4

Foliar treatment test

In a Wagner pot of 1/5000 a. charged with upland field soil, soybean, wheat, corn; nutgrass, yellow-cyperus, watergrass and large crabgrass were grown. At the 2- or 3-leaf stage of wheat, a wettable powder containing 25% of each test compound, prepared as in the above Example 1, was applied by spraying on the foliage at a rate of 300 g.-a.i./10a. Using water as a dispersant at a rate of 10 l/a. The pot was placed in a green house. On the 21st day after treatment, herbicidal activities and phytotoxicities were evaluated on the basis of the scale defined in Example 3. The results are given in the following Table 4.

TABLE 4

| Test comp. No. | Phytotoxicity to crop | | | Herbicidal activity | | | |
|---|---|---|---|---|---|---|---|
| | Soy-bean | Wheat | Corn | Nut-grass | Yellow-cyperus | Water-grass | Large crabgrass |
| 6 | 0 | 0 | 0 | 3 | 3 | 4 | 4 |
| 8 | 0 | 0 | 0 | 2 | 3 | 3 | 3 |
| 9 | 0 | 0 | 0 | 2 | 2 | 3 | 3 |
| 10 | 0 | 0 | 0 | 1 | 2 | 3 | 3 |
| 11 | 0 | 1 | 1 | 4 | 4 | 3 | 4 |
| 12 | 0 | 0 | 0 | 2 | 3 | 2 | 2 |
| 14 | 0 | 0 | 0 | 0 | 2 | 2 | 2 |
| 18 | 0 | 1 | 0 | 4 | 4 | 5 | 5 |
| 19 | 0 | 0 | 1 | 3 | 3 | 4 | 4 |
| 21 | 0 | 0 | 1 | 3 | 3 | 4 | 4 |
| 23 | 0 | 0 | 0 | 4 | 4 | 3 | 4 |
| 25 | 0 | 0 | 0 | 2 | 3 | 3 | 3 |
| 26 | 0 | 0 | 0 | 1 | 1 | 2 | 2 |
| 27 | 0 | 0 | 0 | 1 | 2 | 2 | 2 |
| 28 | 0 | 0 | 0 | 2 | 2 | 3 | 3 |
| 30 | 0 | 0 | 0 | 3 | 3 | 5 | 5 |
| 32 | 0 | 0 | 1 | 3 | 3 | 4 | 5 |
| 36 | 1 | 0 | 0 | 2 | 2 | 1 | 1 |
| 37 | 1 | 0 | 0 | 1 | 1 | 2 | 3 |
| 38 | 0 | 0 | 0 | 3 | 3 | 2 | 3 |
| 40 | 0 | 1 | 0 | 2 | 2 | 3 | 3 |
| 43 | 0 | 0 | 0 | 2 | 3 | 3 | 3 |
| 44 | 0 | 0 | 0 | 2 | 2 | 4 | 4 |
| 45 | 0 | 0 | 1 | 3 | 4 | 4 | 4 |
| 46 | 0 | 0 | 0 | 3 | 3 | 3 | 4 |
| 47 | 0 | 0 | 0 | 1 | 1 | 2 | 2 |
| 49 | 0 | 0 | 0 | 2 | 2 | 3 | 3 |
| 51 | 0 | 0 | 0 | 2 | 3 | 4 | 4 |
| 52 | 0 | 0 | 0 | 3 | 3 | 3 | 3 |
| 61 | 0 | 0 | 0 | 4 | 4 | 3 | 3 |
| 63 | 0 | 1 | 1 | 2 | 2 | 3 | 4 |
| 64 | 0 | 0 | 0 | 1 | 1 | 2 | 2 |
| 68 | 0 | 0 | 0 | 4 | 4 | 4 | 3 |
| 70 | 0 | 0 | 0 | 3 | 4 | 4 | 4 |
| 73 | 0 | 0 | 0 | 2 | 3 | 3 | 3 |
| 76 | 0 | 0 | 0 | 2 | 2 | 2 | 2 |
| 77 | 0 | 0 | 0 | 3 | 3 | 3 | 4 |
| 78 | 0 | 0 | 0 | 2 | 3 | 3 | 4 |
| 79 | 0 | 0 | 0 | 1 | 1 | 2 | 2 |
| 80 | 0 | 0 | 0 | 2 | 2 | 4 | 4 |
| 83 | 0 | 0 | 0 | 4 | 4 | 5 | 5 |
| 84 | 1 | 0 | 0 | 2 | 2 | 3 | 3 |
| 86 | 0 | 0 | 0 | 2 | 2 | 4 | 4 |
| 95 | 0 | 0 | 0 | 3 | 3 | 4 | 4 |
| 96 | 0 | 0 | 1 | 3 | 3 | 4 | 5 |
| 97 | 0 | 0 | 0 | 2 | 3 | 4 | 4 |
| 98 | 0 | 0 | 0 | 3 | 3 | 2 | 2 |

TABLE 4-continued

| Test comp. No. | Phytotoxicity to crop | | | Herbicidal activity | | | |
|---|---|---|---|---|---|---|---|
| | Soy-bean | Wheat | Corn | Nut-grass | Yellow-cyperus | Water-grass | Large crabgrass |
| a ① | 0 | 0 | 0 | 1 | 1 | 1 | 1 |
| b ② | 0 | 0 | 0 | 1 | 0 | 0 | 1 |
| c ③ | 0 | 0 | 0 | 0 | 1 | 1 | 1 |

① - ③ : control compounds a, b and c described above.

EXAMPLE 5

Upland soil treatment test

In a Wagner pot of 1/5000 a. charged with upland field soil, seeds of soybean, wheat and corn and a tuber of nutgrass were placed on the soil and then covered with a small amount of soil. Seeds of yellow-cyperus, watergrass and large crabgrass were also injected in the neighborhood of soil surface. A wettable powder containing 25% of each test compound, prepared as in the above Example 1, was applied by spraying on to the soil surface at a rate of 500 g.-a.i./10a. using water as a dispersant at a rate of 10 l/a. On the 21st day after treatment, herbicidal activities and phytotoxicities were evaluated on the basis of the scale defined in Example 3. The results are given in the following Table 5.

TABLE 5

| Test comp. No. | Phytotoxicity to crop | | | Herbicidal activity | | | |
|---|---|---|---|---|---|---|---|
| | Soy-bean | Wheat | Corn | Nut-grass | Yellow-cyperus | Water-grass | Large crabgrass |
| 1 | 0 | 0 | 0 | 4 | 5 | 2 | 3 |
| 4 | 0 | 0 | 0 | 3 | 3 | 2 | 3 |
| 5 | 0 | 0 | 0 | 2 | 4 | 3 | 4 |
| 6 | 0 | 0 | 0 | 3 | 4 | 2 | 3 |
| 11 | 0 | 0 | 1 | 1 | 3 | 4 | 4 |
| 16 | 0 | 0 | 0 | 1 | 3 | 2 | 4 |
| 18 | 0 | 1 | 0 | 2 | 3 | 3 | 4 |
| 19 | 0 | 0 | 0 | 4 | 4 | 5 | 5 |
| 23 | 0 | 0 | 0 | 3 | 3 | 3 | 4 |
| 24 | 0 | 0 | 0 | 4 | 4 | 4 | 5 |
| 25 | 0 | 1 | 0 | 3 | 4 | 4 | 5 |
| 27 | 0 | 0 | 0 | 2 | 4 | 4 | 4 |
| 29 | 0 | 0 | 0 | 2 | 2 | 4 | 3 |
| 34 | 0 | 0 | 0 | 3 | 3 | 0 | 2 |
| 36 | 1 | 0 | 0 | 3 | 4 | 0 | 1 |
| 37 | 1 | 0 | 0 | 3 | 4 | 4 | 4 |
| 38 | 0 | 0 | 0 | 3 | 4 | 2 | 3 |
| 40 | 0 | 1 | 1 | 3 | 4 | 4 | 5 |
| 41 | 0 | 0 | 1 | 2 | 3 | 4 | 4 |
| 42 | 0 | 0 | 0 | 2 | 2 | 0 | 1 |
| 44 | 0 | 0 | 0 | 3 | 4 | 0 | 1 |
| 48 | 0 | 0 | 0 | 4 | 4 | 2 | 3 |
| 51 | 0 | 0 | 0 | 4 | 5 | 2 | 2 |
| 52 | 0 | 0 | 0 | 2 | 3 | 0 | 0 |
| 53 | 1 | 1 | 0 | 3 | 4 | 2 | 3 |
| 56 | 0 | 0 | 0 | 2 | 3 | 0 | 2 |
| 62 | 0 | 1 | 0 | 4 | 4 | 4 | 5 |
| 63 | 0 | 1 | 1 | 3 | 4 | 3 | 4 |
| 64 | 0 | 0 | 0 | 2 | 3 | 4 | 4 |
| 65 | 0 | 0 | 0 | 1 | 2 | 2 | 3 |
| 67 | 0 | 1 | 1 | 2 | 2 | 2 | 3 |
| 68 | 0 | 0 | 0 | 1 | 2 | 2 | 3 |
| 73 | 0 | 0 | 0 | 2 | 3 | 2 | 3 |
| 75 | 0 | 0 | 0 | 1 | 2 | 3 | 3 |
| 76 | 0 | 0 | 1 | 3 | 4 | 4 | 5 |
| 77 | 0 | 1 | 0 | 1 | 2 | 0 | 0 |
| 78 | 0 | 0 | 0 | 3 | 4 | 3 | 4 |
| 88 | 0 | 0 | 0 | 2 | 3 | 3 | 4 |
| 90 | 0 | 0 | 0 | 2 | 3 | 2 | 2 |
| 91 | 0 | 0 | 0 | 3 | 3 | 2 | 2 |
| a ① | 0 | 0 | 0 | 3 | 1 | 1 | 1 |
| b ② | 0 | 0 | 0 | 1 | 1 | 1 | 1 |

TABLE 5-continued

| Test comp. No. | Phytotoxicity to crop | | | Herbicidal activity | | | |
|---|---|---|---|---|---|---|---|
| | Soybean | Wheat | Corn | Nutgrass | Yellow-cyperus | Water-grass | Large crabgrass |
| c ③ | 0 | 0 | 1 | 1 | 1 | 0 | 1 |

① – ③ : control compounds a, b and c described above.

EXAMPLE 6

Paddy filed test

A paddy field was partitioned with poly(vinyl chloride) sheet into some parts, each part being 1 m². Seeds of barnyardgrass, three-squaregrass and umbrellaplant and tubers of water nutgrass and water chestnut were injected in the neighborhood of soil surface in each part. Eight hills, having three seedlings, of paddy rice were also transplanted. On the 3rd day after transplanting of paddy rice seedlings, a water dispersion of wettable powder containing 25% of each test compound, prepared as in the above Example 1, was applied by dripping on to the surface of water at rates of 100 g.-, 200 g.- and 400 g.-a.i./10a. On the 30th day after treatment, herbicidal activities and phytotoxocities were evaluated on the basis of the scale defined in Example 3. The results are given in the following Table 6.

TABLE 6

| Test comp. No. | Dose (g-a.i./10a) | Phytotoxicity to rice | Herbicidal activity | | | | |
|---|---|---|---|---|---|---|---|
| | | | Barnyardgrass | Three-squaregrass | Umbrellaplant | Water nutgrass | Water chestnut |
| 1 | 400 | 0 | 5 | 5 | 5 | 5 | 5 |
| | 200 | 0 | 5 | 5 | 5 | 5 | 5 |
| | 100 | 0 | 4 | 5 | 5 | 5 | 5 |
| 2 | 400 | 0 | 5 | 5 | 5 | 5 | 5 |
| | 200 | 0 | 4 | 5 | 5 | 5 | 4 |
| | 100 | 0 | 4 | 4 | 5 | 3 | 3 |
| 4 | 400 | 0 | 5 | 5 | 5 | 5 | 4 |
| | 200 | 0 | 4 | 4 | 5 | 4 | 3 |
| | 100 | 0 | 3 | 3 | 4 | 3 | 2 |
| 5 | 400 | 0 | 5 | 5 | 5 | 5 | 4 |
| | 200 | 0 | 4 | 4 | 4 | 3 | 3 |
| | 100 | 0 | 2 | 3 | 2 | 2 | 2 |
| 11 | 400 | 0 | 5 | 5 | 5 | 5 | 5 |
| | 200 | 0 | 5 | 5 | 5 | 5 | 4 |
| | 100 | 0 | 3 | 5 | 5 | 4 | 3 |
| 19 | 400 | 0 | 5 | 5 | 5 | 5 | 4 |
| | 200 | 0 | 4 | 4 | 4 | 4 | 3 |
| | 100 | 0 | 3 | 4 | 4 | 3 | 1 |
| 24 | 400 | 0 | 5 | 5 | 5 | 5 | 4 |
| | 200 | 0 | 5 | 4 | 4 | 4 | 3 |
| | 100 | 0 | 4 | 3 | 4 | 3 | 2 |
| 36 | 400 | 0 | 5 | 5 | 5 | 5 | 5 |
| | 200 | 0 | 3 | 5 | 5 | 5 | 5 |
| | 100 | 0 | 2 | 5 | 5 | 5 | 4 |
| 37 | 400 | 0 | 5 | 5 | 5 | 5 | 5 |
| | 200 | 0 | 4 | 5 | 5 | 5 | 5 |
| | 100 | 0 | 3 | 5 | 5 | 5 | 5 |
| 41 | 400 | 0 | 5 | 5 | 5 | 5 | 4 |
| | 200 | 0 | 5 | 2 | 5 | 5 | 3 |
| | 100 | 0 | 4 | 2 | 3 | 3 | 2 |
| 42 | 400 | 0 | 3 | 5 | 5 | 5 | 4 |
| | 200 | 0 | 2 | 4 | 5 | 5 | 3 |
| | 100 | 0 | 1 | 3 | 4 | 3 | 2 |
| 44 | 400 | 0 | 2 | 5 | 5 | 4 | 3 |
| | 200 | 0 | 0 | 5 | 5 | 2 | 2 |
| | 100 | 0 | 0 | 5 | 4 | 2 | 1 |
| 53 | 400 | 0 | 5 | 5 | 5 | 5 | 5 |
| | 200 | 0 | 4 | 5 | 5 | 5 | 4 |
| | 100 | 0 | 3 | 5 | 5 | 4 | 2 |
| 57 | 400 | 0 | 4 | 5 | 5 | 5 | 5 |
| | 200 | 0 | 3 | 5 | 5 | 5 | 4 |
| | 100 | 0 | 2 | 4 | 4 | 3 | 2 |
| 77 | 400 | 0 | 5 | 5 | 5 | 5 | 5 |

TABLE 6-continued

| Test comp. No. | Dose (g-a.i./10a) | Phytotoxicity to rice | Herbicidal activity | | | | |
|---|---|---|---|---|---|---|---|
| | | | Barnyardgrass | Three-squaregrass | Umbrellaplant | Water nutgrass | Water chestnut |
| | 200 | 0 | 4 | 5 | 5 | 5 | 4 |
| | 100 | 0 | 3 | 5 | 5 | 4 | 2 |
| 91 | 400 | 0 | 3 | 5 | 5 | 5 | 4 |
| | 200 | 0 | 2 | 4 | 5 | 4 | 2 |
| | 100 | 0 | 1 | 3 | 4 | 3 | 1 |
| control comp. a | 400 | 3 | 2 | 5 | 4 | 2 | 1 |
| | 200 | 2 | 1 | 4 | 3 | 0 | 0 |
| | 100 | 2 | 1 | 2 | 3 | 0 | 0 |
| control comp. b | 400 | 0 | 2 | 3 | 4 | 3 | 2 |
| | 200 | 0 | 2 | 1 | 2 | 2 | 0 |
| | 100 | 0 | 0 | 0 | 2 | 0 | 0 |
| control comp. c | 400 | 0 | 2 | 3 | 3 | 2 | 3 |
| | 200 | 0 | 0 | 3 | 2 | 1 | 1 |
| | 100 | 0 | 0 | 2 | 2 | 1 | 0 |

What is claimed is:

1. A compound of the formula

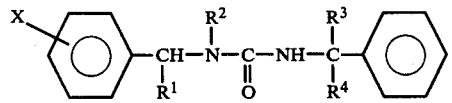

wherein X is selected from the group consisting of a hydrogen atom, a halogen atom, a lower alkyl group and a lower alkoxyl group, $R^1$ is a methyl group or an ethyl group, $R^2$ is a hydrogen atom, a lower alkyl group or an allyl group, $R^3$ is a methyl group or an ethyl group and $R^4$ is an ethyl group.

2. The compound of claim 1, wherein X is in the ortho-position.

3. The compound of claim 1, wherein X is a halogen atom.

4. The compound of claim 1, wherein X is a chlorine atom at the ortho-position.

5. The compound of claim 1, wherein X is a chlorine atom at the ortho-position, $R^1$ is a methyl group, $R^2$ is a hydrogen atom and $R^3$ is an ethyl group.

6. The compound of claim 1, wherein X is a chlorine atom at the ortho-position, each of $R^1$ and $R^2$ is a methyl group and $R^3$ is an ethyl group.

7. The compound of claim 1, wherein X is a chlorine atom at the ortho-position, $R^1$ is a methyl group, $R^2$ is an allyl group and $R^3$ is an ethyl group.

8. The compound of claim 1, wherein X is a lower alkyl group.

9. The compound of claim 1, wherein X is a methyl group at the ortho-position.

10. The compound of claim 1, wherein X is a methyl group at the ortho-position, $R^1$ is a methyl group, $R^2$ is a hydrogen atom and $R^3$ is an ethyl group.

11. The compound of claim 1, wherein X is a methyl group at the ortho-position, each of $R^1$ and $R^2$ is a methyl group and $R^3$ is an ethyl group.

12. The compound of claim 1, wherein X is a methyl group at the ortho-position, $R^1$ is a methyl group, $R^2$ is an allyl group and $R^3$ is an ethyl group.

13. The compound of claim 1, wherein X is a lower alkoxyl group.

14. The compound of claim 1, wherein X is a methoxyl group at the ortho-position.

15. The compound of claim 1, wherein X is a methoxyl group at the ortho-position, $R^1$ is a methyl group, $R^2$ is a hydrogen atom and $R^3$ is an ethyl group.

16. The compound of claim 1, wherein X is a methoxyl group at the ortho-position, each of $R^1$ and $R^2$ is a methyl group and $R^3$ is an ethyl group.

17. The compound of claim 1, wherein X is a methoxyl group at the ortho-position, $R^1$ is a methyl group, $R^2$ is an allyl group and $R^3$ is an ethyl group.

18. The compound of claim 1, wherein X is a hydrogen atom, $R^1$ is a methyl group, $R^2$ is a hydrogen atom and $R^3$ is an ethyl group.

19. The compound of claim 1, wherein X is a hydrogen atom, each of $R^1$ and $R^2$ is a methyl group and $R^3$ is an ethyl group.

20. The compound of claim 1, wherein X is a hydrogen atom, $R^1$ is a methyl group, $R^2$ is an allyl group and $R_3$ is an ethyl group.

21. The compound of claim 1, wherein X is a hydrogen atom, $R^1$ is an ethyl group, $R^2$ is a hydrogen atom and $R^3$ is an ethyl group.

22. The compound of claim 1, wherein X is a hydrogen atom, $R^1$ is an ethyl group, $R^2$ is a methyl group and $R^3$ is an ethyl group.

23. The compound of claim 1, wherein X is a hydrogen atom, $R^1$ is an ethyl group, $R^2$ is an allyl group and $R^3$ is an ethyl group.

24. A herbicidal composition which comprises (i) a herbicidally effective amount of a compound according to any of claims 1–23 and (ii) an agronomically-acceptable carrier.

* * * * *